United States Patent
Trutwig et al.

(10) Patent No.: US 9,287,094 B2
(45) Date of Patent: Mar. 15, 2016

(54) PLASMA TREATMENT DEVICE COMPRISING A ROLLER MOUNTED ROTATABLY IN A HANDLE HOUSING

(71) Applicant: CINOGY GMBH, Duderstadt (DE)

(72) Inventors: Leonhard Trutwig, Duderstadt (DE); Karl-Otto Storck, Duderstadt (DE); Dirk Wandke, Heilbad Heillgenstadt (DE); Matthias Kopp, Gieboldenhausen (DE); Georg Daeschlein, Wandlitz OT Klosterfelde (DE)

(73) Assignee: CYNOGY GmbH, Duderstadt (DE)

( * ) Notice: Subject to any disclaimer, the term of this patent is extended or adjusted under 35 U.S.C. 154(b) by 0 days.

(21) Appl. No.: 14/759,508

(22) PCT Filed: Jan. 2, 2014

(86) PCT No.: PCT/DE2014/000001
§ 371 (c)(1),
(2) Date: Jul. 7, 2015

(87) PCT Pub. No.: WO2014/111081
PCT Pub. Date: Jul. 24, 2014

(65) Prior Publication Data
US 2015/0357163 A1     Dec. 10, 2015

(30) Foreign Application Priority Data
Jan. 15, 2013   (DE) .......................... 10 2013 000 440

(51) Int. Cl.
*H05H 1/46*       (2006.01)
*H01J 37/32*     (2006.01)

(52) U.S. Cl.
CPC ................................ *H01J 37/32348* (2013.01)

(58) Field of Classification Search
CPC   B29C 2059/145; B29C 59/106; B29C 59/14; H01J 37/32935
USPC .......................................................... 313/48
See application file for complete search history.

(56) References Cited

U.S. PATENT DOCUMENTS

| 5,711,814 | A  |   | 1/1998  | Mori |
|-----------|----|---|---------|------|
| 8,557,187 | B2 | * | 10/2013 | Ehlbeck .................. B29C 59/14 422/130 |
| 9,120,334 | B2 | * | 9/2015  | Nagai .................. B41J 11/0015 |
| 2009/0098311 | A1 |  | 4/2009 | Aomine et al. |
| 2009/0120782 | A1 |  | 5/2009 | Hammen et al. |

FOREIGN PATENT DOCUMENTS

| DE | 3831964 A1       | 6/1989  |
|----|------------------|---------|
| DE | 102009060627 A1  | 6/2011  |
| DE | 102011105713 A1  | 12/2012 |
| DE | 102012103470 A1  | 10/2013 |
| JP | 2003142415       | 5/2003  |
| WO | 2006116252 A2    | 11/2006 |
| WO | 2009003613 A1    | 1/2009  |
| WO | 2009003616 A1    | 1/2009  |
| WO | 2011076193 A1    | 6/2011  |
| WO | 2012053083 A1    | 4/2012  |
| WO | 2013156352 A2    | 10/2013 |

OTHER PUBLICATIONS

"Plasma-Roller_MM-1540-HAWK" MBM Sciencebridge GmbH (2 pages from the Internet).

* cited by examiner

*Primary Examiner* — Tracie Y Green
(74) *Attorney, Agent, or Firm* — Whitham Curtis Christofferson & Cook, PC

(57) ABSTRACT

A plasma treatment device for treating a surface with a dielectrically impeded plasma field which is generated between an electrode (16), to which a high voltage is supplied, and the surface, wherein the electrode (16) forms, with a dielectric (17) surrounding the electrode (16), a roller (6) mounted rotatably in a grip housing (1), which roller can be rolled on the surface, has an extended treatment field and enables defined and controlled plasma treatment of the surface by virtue of the fact that the roller (6) is designed such that it can be matched flexibly to irregularities on the surface and has a rolling area with elevations (19, 19'), between which interspaces (20) forming the plasma field are located.

9 Claims, 4 Drawing Sheets

PLASMA TREATMENT DEVICE COMPRISING A ROLLER MOUNTED ROTATABLY IN A HANDLE HOUSING

The invention relates to a plasma treatment device for treating a surface with a dielectric barrier plasma field, which is generated between an electrode supplied with high voltage and the surface, the electrode with a dielectric enclosing the electrode forming a roller mounted rotatably in a handle housing, which can be rolled on the surface.

The treatment of surfaces with a plasma is known for a wide variety of surfaces. For instance, plastic surfaces which, without pretreatment, cannot be coated, for example lacquered, or can be coated only with difficulty, can be coated substantially better after a plasma treatment. Similar considerations apply for keratin surfaces, for example hairs, which can take up treatment or care products substantially better after a plasma treatment. It is furthermore known to disinfect surfaces with a plasma treatment. Plasma treatment is also possible on the living body, in order to improve the ability of the skin to take up care products and medicaments, in particular for healing, and to disinfect affected surfaces.

While the plasma field can be generated directly between two electrodes for plasma treatment for material processing, in many cases it is expedient to provide a so-called dielectric barrier plasma discharge. In dielectric barrier plasma discharge, air or another gas is ionized by a high-voltage field, but the flow of current resulting in principle because of the high potential differences is prevented by a dielectric arranged in between. It is therefore known to embed a high-voltage electrode in the dielectric in order to reliably prevent current arcing and to produce the plasma field with a counter electrode, in which case the surface to be treated may be used as the counter electrode, which is usually grounded, when the material of the surface to be treated is electrically conductive. WO 2011/076193 A1 discloses a flat arrangement consisting of a flat electrode embedded in a flexible dielectric, which can be applied onto a surface and which because of its flexibility can adapt to a certain extent to irregularities of the surface. The surface of the electrode arrangement is in this case provided with bump-like elevations in order to ensure, during application onto the surface to be treated, air spaces in which the plasma can form in the interspaces between the elevations. Such an arrangement is not universally usable, since the size of the electrode arrangement needs to be adapted to the size of the surface to be treated, in order to allow realistic treatment of the surface.

An Internet publication of MBM ScienceBridge GmbH, Göttingen discloses a so-called plasma roller, which consists of a ceramic-clad copper tube as an electrode. The roller is guided over the surface to be treated in the manner of a paint roller, so that it forms a linear contact with the surface. The plasma field is evidently formed on both sides of the linear contact. The plasma roller is intended to be suitable for disinfecting walls, floors or pieces of furniture, and for pretreatment of these objects for painting or other coatings without solvents and primers, when the plasma roller is guided repeatedly over the surface to be treated.

The previously known design of the plasma roller is suitable only for smooth surfaces, and has the disadvantage that plasma fields decreasing greatly as a function of the distance to the contact line of the plasma roller with the surface are formed, so that controlled and defined plasma treatment is not possible.

It is therefore the object of the present invention to widen the range of use of an electrode arrangement configured as a roller for plasma treatment, and to allow better-defined and better-controlled plasma treatment.

In order to achieve this object, a plasma treatment device of the type mentioned in the introduction is characterized according to the invention in that the roller is configured to be flexibly adaptable to irregularities of the surface and has a rolling surface with elevations, between which interspaces are located wherein the plasma field can be formed.

The plasma treatment device according to the invention therefore has a roller which can adapt flexibly to irregularities of the surface. To this end, the dielectric is formed in particular from a highly flexible plastic and preferably with a Shore A hardness of between 30 and 60. Suitable highly flexible materials are thermoplastic elastomers (TPE). A plasma treatment device according to the invention can therefore already be adaptable to the irregularities of the surface by the highly flexible configuration of the dielectric, even if the electrode itself is rigid. In a preferred embodiment of the invention, however, the electrode is also configured to be flexible, and therefore consists of a flexible material, is mounted rotatably with rigid endpieces in the handle housing. The mounting is preferably carried out at both ends of the electrode. Also possible, however, is unilateral mounting of the electrode, which can therefore be configured with one free end.

According to the invention, the surface of the roller is furthermore provided with elevations, between which there are interspaces in which the plasma field is formed. The roller in this case has very many elevations, which may be arranged regularly or irregularly on the surface. The interspaces between the elevations are preferably connected to one another, so that a uniform gas space can be formed around the elevations when the roller bears—optionally under pressure—on the surface to be treated. Owing to the soft configuration of the dielectric, and optionally the flexibility of the electrode, a relatively wide plasma field is also formed in the contact region between the roller and the surface to be treated, this plasma field only being interrupted at the bearing points, which do not form an uninterrupted line but only form, along a contact strip between the surface of the roller and the surface to be treated, point contact surfaces between which a plasma field can be formed in a interspace between the contact points. Since the position of the contact points changes constantly during the rolling, a relatively wide plasma field is thus obtained with an approximately homogeneous field strength, by which controlled and defined plasma treatment of the surface is possible.

The plasma treatment device according to the invention is suitable for all the fields of application mentioned above, for which the known plasma devices are suitable. Furthermore, the plasma treatment device according to the invention makes it possible to treat uneven surfaces of any size, still with a better-defined plasma treatment. This is important in particular for plasma treatment of the skin of a living body, since controlled treatment, for example of the facial skin or the skin on other parts of the body, is made possible by a plasma treatment device according to the invention with a suitably selected roller size.

The preferred flexibility of the electrode itself may be achieved by various embodiments of the invention. In a particularly preferred embodiment, the electrode consists of a resilient material with rigid endpieces, in which case the endpieces may be used for rotatable mounting as well as for electrical contacting. To this end, at least one of the rigid endpieces is configured to be electrically conductible and contactable by the high-voltage source.

The resilient material may be a coil spring, so that the electrode is formed from a hollow coil spring.

In other embodiments, the flexible configuration of the electrode may also be formed by solid resilient materials which are electrically conductive. It is furthermore possible for the resilience to be ensured by a tubular sleeve of the electrode, which may be filled with an electrically conductive material, also in the form of a liquid. The liquid in this case forms the conductive part of the electrode, while the resilient sleeve may be conductive, but does not have to be. In this case, it would also be envisionable to configure the resilient sleeve as the dielectric, in which there is a deformable conductive material with which the defined high-voltage potential is brought to a distance, defined by the dielectric, from the surface to be treated.

In a preferred embodiment, the handle housing encloses the roller almost completely and may leave only a small opening, out of which only a small circumferential section of the roller protrudes. The protruding circumferential section may in this case therefore extend over an angle of from 20 to 120°.

In a variant of the invention, the handle housing may also support a plurality of rollers, which are guided successively in the movement direction over the surface to be treated. It is furthermore possible to construct a roller from a plurality of subrollers over its axial length.

The invention will be explained in more detail below with the aid of exemplary embodiments.

Figure 1:
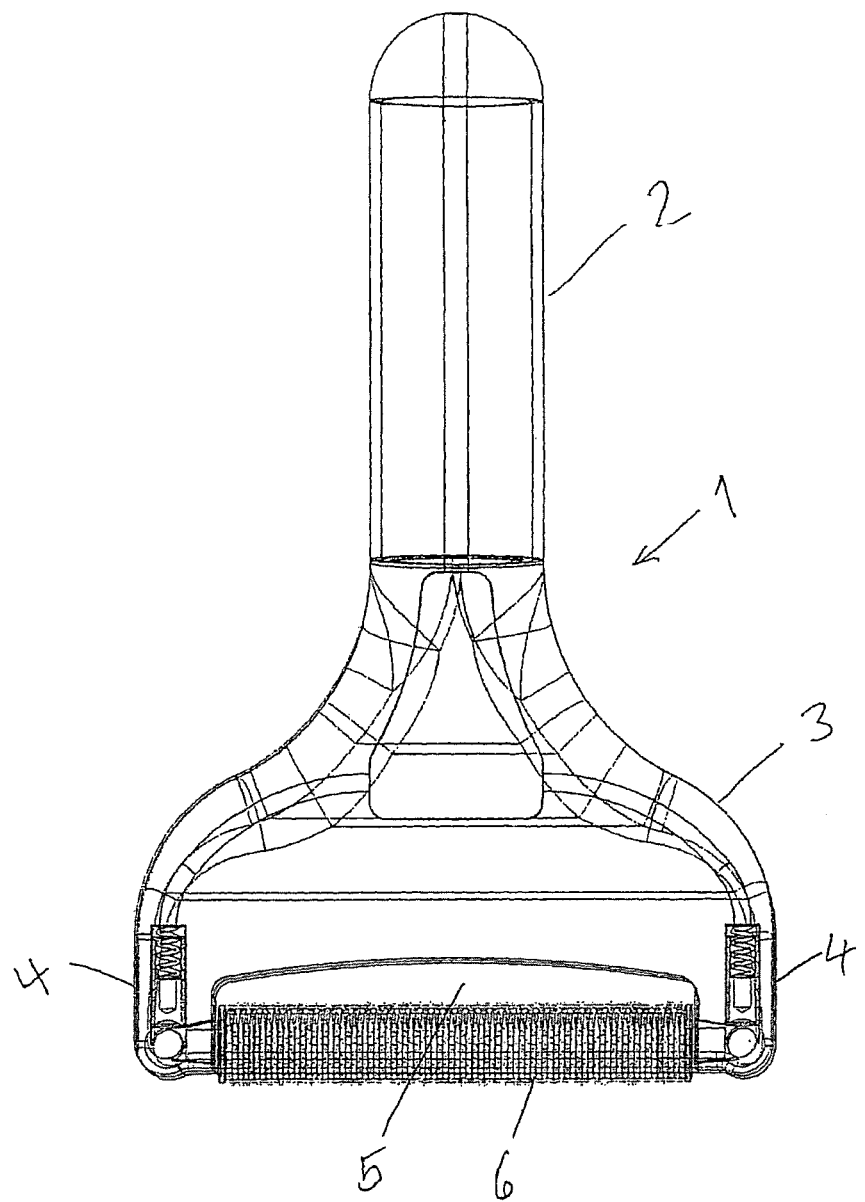
FIG. 1 shows a partially cut-away overall representation of a plasma treatment device according to the invention.

As shown by the exemplary embodiment according to FIG. 1, the plasma treatment device may have a handle housing 1, which comprises a handle section 2 and a holding section 3. The handle section 2 is suitable for being gripped by a hand, and may be provided with conventional nonslip surfaces ensuring gripping.

The holding section 3 comprises two parallel branches 4 extending away from the handle section 2, between which there is a free space 5. An electrode arrangement in the form of a roller 6 is rotatably mounted at the ends of the branches 4, as will be explained in more detail below. The roller 6 fitted into the free space 5 is almost entirely covered on its upper side and lower side by the handle housing 1, and protrudes only with a small circumferential section of the roller 6 out of the handle housing 1. The effect of this is that the handle housing 1 with the handle section 2 must be held essentially perpendicularly to the surface to be treated so that a circumferential section of the roller obtains the desired contact with the surface (not represented) to be treated.

Figure 2:
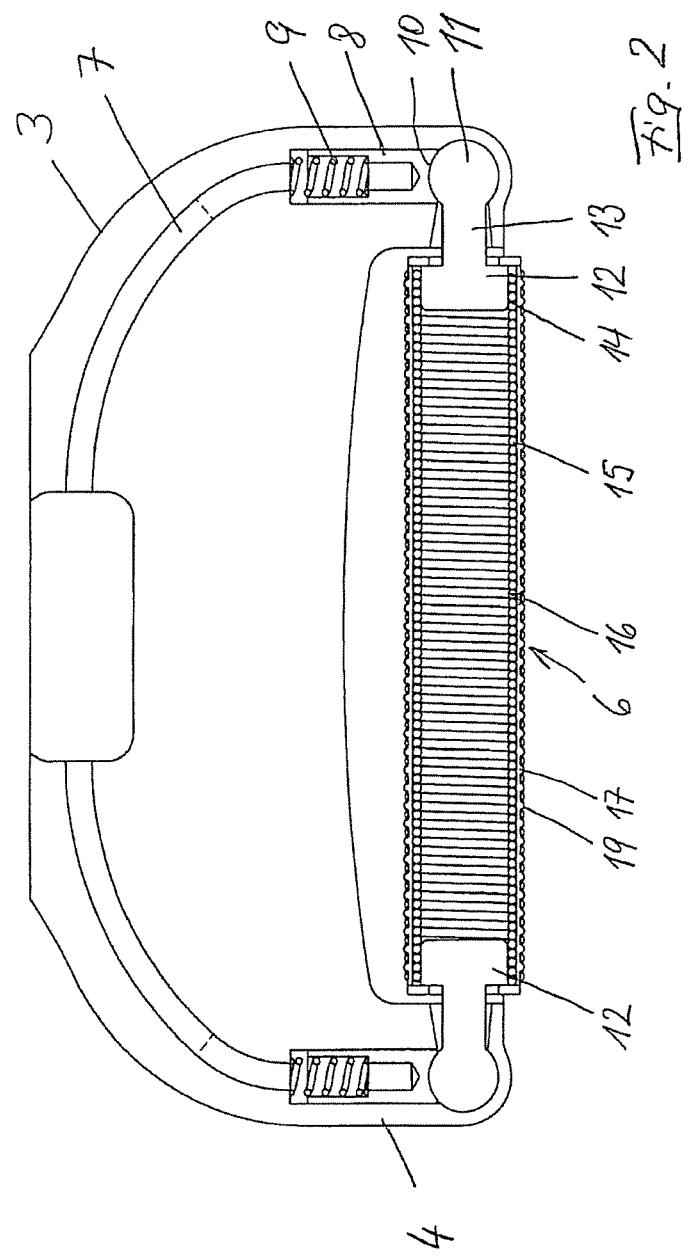
FIG. 2 shows an enlarged representation of a first embodiment of a roller with a flexible electrode.

FIG. 2 shows an enlarged sectional representation of some design details of the holding section 3 of the handle housing 1 and of the roller 6 in a first embodiment. Extending in the direction of the two branches 4, the holding section 3 has channels 7 in which high-voltage lines are fed. These are connected to a hollow metal cylinder 8, which is guided axially displaceable to some extent in an associated chamber of the holding section 3. A compression spring 9 braced in the hollow cylinder 8 presses the hollow cylinder, which has a concave end surface 10, against a spherical section 11 of a metal endpiece 12 of the roller 6. The metal endpiece 12 is connected in a rotationally fixed fashion to the roller 6 and is rotatably mounted with a cylindrical section 13 in a corresponding channel of the holding section 3. Accordingly, the spherical section 11 can rotate relative to the concave end surface 10, the electrical contact being maintained by the pressure of the compression spring 9.

The endpiece 12 protrudes with a bolt section 14, having a larger diameter than the cylindrical section 3, and in a matching fashion into a hollow cylindrical arrangement of a coil spring 15, which is terminated at its two ends by a metal endpiece 12 and is mounted rotatably in the holding section 3 of the handle housing 1. Between the two endpieces 12, the coil spring 15 is configured with turns of the coil spring bearing on one another. The coil spring 15 forms with the metal endpieces 12 an elongate rotatably mounted electrode 16, which can be locally deflected by virtue of the coil spring 15 by irregularities of the surface to be treated and thereby follow curvatures of the surface to be treated during the rolling.

The electrode 16 formed in this way is enclosed over its entire lateral surface by a tubular dielectric 17. The dielectric 17 consists of a flexible material, which allows and participates in the described deformation of the flexible electrode. The dielectric 17 is respectively terminated at the two extreme ends by an annular disk 18, which respectively has a through-opening allowing the cylindrical section 13 to pass through and on which the respective end of the coil spring 15 can be braced.

The dielectric 17 consists of a highly flexible material, preferably of TPE, and has elevations 19 in the form of small protruding bumps on its outer surface.

Figure 3:
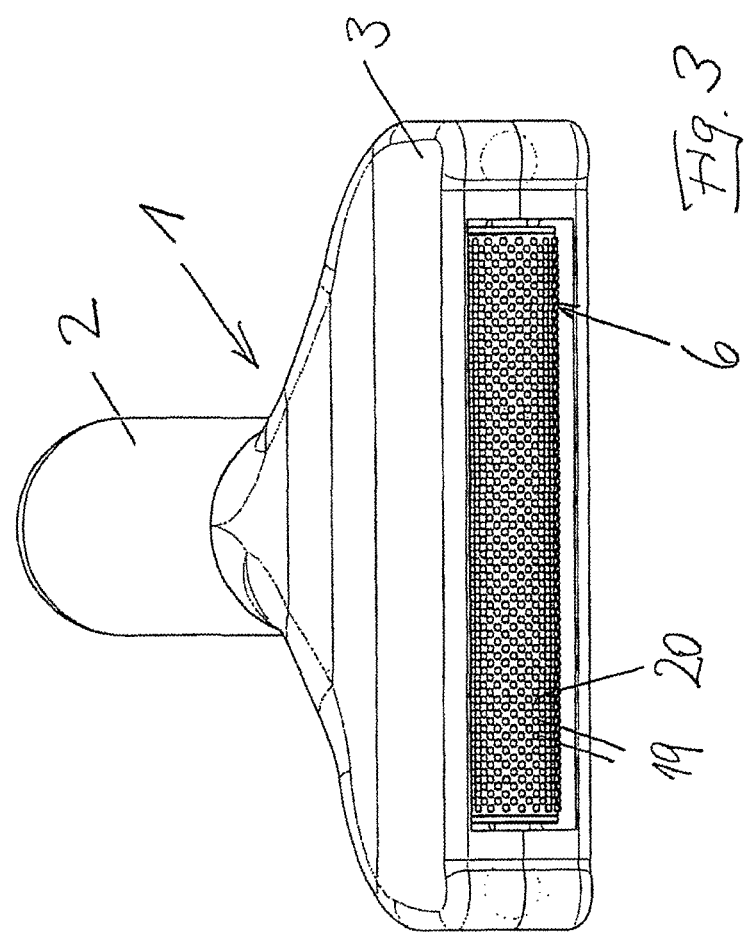
FIG. 3 shows a representation of the plasma treatment device according to FIG. 1 in a view of the surface of an exemplary embodiment of a dielectric.

The view of FIG. 3 illustrates that the elevations 19 are small dome-like bumps, which approximately have the shape of a hemisphere, in which case the radius of the bumps may preferably lie between 0.2 and 0.5 mm, so that there is a bump diameter of from 0.4 to 1.0 mm and a height of the bumps between 0.2 and 0.5 mm. In the exemplary embodiment represented in FIG. 3, the elevations 19 are arranged axially aligned in rows, the elevations 19 of neighboring axial lines being arranged offset with respect to one another. This leads to a respective interspace 20 between two bumps (in any direction) which also corresponds approximately to the bump diameter or may be slightly larger. The interspaces 20 are connected to one another, so that no cells closed by elevations 19 are formed on the surface. Such an arrangement, for example with honeycombed elevations, would also be possible, but is not preferred as an embodiment.

Figure 4:
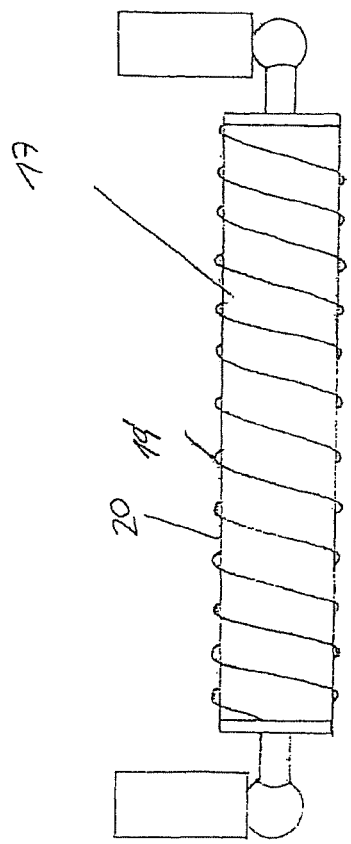
FIG. 4 shows a schematic view of a second exemplary embodiment of a roller configured according to the invention.
Figure 5:
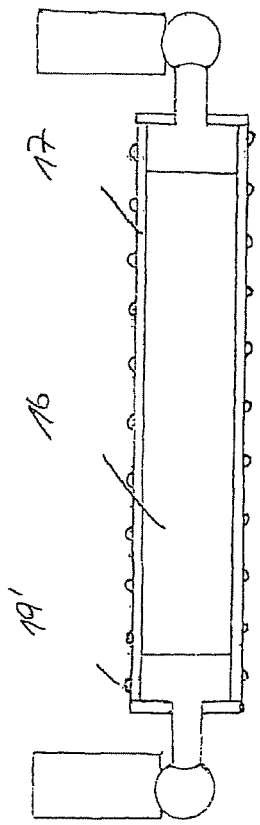
FIG. 5 shows a sectional representation through the roller according to FIG. 4.

The embodiment of an electrode 16 as represented in FIGS. 4 and 5 differs from the embodiment in FIGS. 2 and 3 merely in that the dielectric 17 elevations 19' are formed in the shape of a wire extending around in a spiral at large distances, which is connected to the surface of the dielectric 17. The elevations 19' in the form of the wire may be formed integrally with the dielectric 17 or applied afterwards onto the surface of the dielectric 17. The material of the elevation 19' may be any material, when the elevation 19' is formed separately from the dielectric 17. The elevation 19' may consist of a conductive or, preferably, nonconductive material. As a conductive material, the elevation 19' would assume the ground potential when it comes in contact with the grounded surface to be treated. A flow of current from the elevation 19' to the electrode 16 is reliably prevented by the dielectric 17.

It can be seen that the elevations 19' on the surface of a dielectric 17 could be applied straightforwardly afterwards and fixed there, so as to establish the distance between the surface of the dielectric 17 and the surface to be treated, in which there is a defined air space for formation of the plasma field. It can furthermore be seen that, when the roller 6 rolls on the surface to be treated, the respective contact points between the elevation 19' and the surface to be treated migrate, so that a uniform plasma treatment of the surface is ensured.

The exemplary embodiments represented are in no way meant to be restrictive. Other shapes and patterns of the elevations 19, 19' may readily be produced within the scope of the invention. Furthermore, the dimensioning according to aspects known to the person skilled in the art, as to which height of the elevations 19, 19' is expediently provided for the respective treatment passed, is left open. In general, however, an elevation of between 0.2 and 1.5 mm will be appropriate. The area occupied by the elevations 19, 19' should occupy a proportion of from 1 to 15% in terms of the area of the interspaces 20. What is essential in this case is that the elevations 19, 19' always lead to point-like or small-area contacts with the surface to be treated, and sizeable continuous contact surfaces are avoided.

The invention claimed is:

1. A plasma treatment device for treating a surface with a dielectric barrier plasma field, comprising
    an electrode supplied with high voltage;
    a dielectric enclosing the electrode forming a roller; and
    a handle housing, wherein the roller is mounted rotatably in the handle housing and which can be rolled on the surface, wherein the roller is configured to be flexibly adaptable to irregularities of the surface and has a rolling surface with elevations with interspaces therebetween for forming the plasma field between the electrode and the surface.

2. The plasma treatment device as claimed in claim 1, wherein the interspaces are connected to one another.

3. The plasma treatment device as claimed in claim 1, wherein the dielectric is of a highly flexible plastic.

4. The plasma treatment device as claimed in claim 3, wherein the highly flexible plastic has a Shore (A) hardness of between 30 and 60.

5. The plasma treatment device as claimed in claim 1 wherein the roller includes two ends and wherein the roller is mounted rotatably with each of said two ends in the handle housing.

6. The plasma treatment device as claimed in claim 1 wherein the electrode is flexible.

7. The plasma treatment device as claimed in claim 6, wherein the electrode is formed from a resilient material with rigid endpieces.

8. The plasma treatment device as claimed in claim 7, wherein the resilient material is a coil spring.

9. The plasma treatment device as claimed in claim 7, wherein at least one of the rigid endpieces is electrically conductive and contactable by a high-voltage source.

* * * * *